United States Patent
Ito et al.

(10) Patent No.: US 12,083,152 B2
(45) Date of Patent: Sep. 10, 2024

(54) AGENT FOR IMPROVING MITOCHONDRIAL FUNCTION

(71) Applicants: MEIJI CO., LTD., Tokyo (JP); NATIONAL UNIVERSITY CORPORATION HAMAMATSU UNIVERSITY SCHOOL OF MEDICINE, Shizuoka (JP)

(72) Inventors: Takashi Ito, Hamamatsu (JP); Mitsutoshi Setou, Hamamatsu (JP); Satoru Ozaki, Tokyo (JP); Chinami Mizoguchi, Tokyo (JP); Yukio Asami, Tokyo (JP)

(73) Assignees: MEIJI CO., LTD., Tokyo (JP); NATIONAL UNIVERSITY CORPORATION HAMAMATSU UNIVERSITY SCHOOL OF MEDICINE, Shizuoka (JP)

(*) Notice: Subject to any disclaimer, the term of this patent is extended or adjusted under 35 U.S.C. 154(b) by 171 days.

(21) Appl. No.: 17/279,941

(22) PCT Filed: Sep. 26, 2019

(86) PCT No.: PCT/JP2019/038014
§ 371 (c)(1),
(2) Date: Sep. 20, 2021

(87) PCT Pub. No.: WO2020/067368
PCT Pub. Date: Apr. 2, 2020

(65) Prior Publication Data
US 2022/0008489 A1 Jan. 13, 2022

(30) Foreign Application Priority Data
Sep. 26, 2018 (JP) .................... 2018-180969

(51) Int. Cl.
A61K 35/747 (2015.01)
A23L 33/135 (2016.01)

(52) U.S. Cl.
CPC .......... *A61K 35/747* (2013.01); *A23L 33/135* (2016.08)

(58) Field of Classification Search
CPC ...... A61K 35/747; A61K 35/744; A61K 8/99; A23L 33/135; A61P 3/00; A61P 25/00; A61P 25/26; A61P 17/00; A61P 25/28; A61P 43/00; A61Q 19/08; C12N 1/20
See application file for complete search history.

(56) References Cited

U.S. PATENT DOCUMENTS

| | | | |
|---|---|---|---|
| 10,028,983 B2 | 7/2018 | Yamamoto et al. | |
| 10,226,441 B2 | 3/2019 | Higashi et al. | |
| 2004/0047896 A1* | 3/2004 | Malnoe | A61P 9/00 514/5.5 |
| 2005/0100617 A1 | 5/2005 | Malnoe et al. | |
| 2005/0244389 A1 | 11/2005 | Fioramonti et al. | |
| 2007/0020328 A1 | 1/2007 | Lin | |
| 2009/0263366 A1 | 10/2009 | Lin | |
| 2011/0091431 A1 | 4/2011 | Olmstead | |
| 2015/0246082 A1 | 9/2015 | Lin | |

FOREIGN PATENT DOCUMENTS

| | | |
|---|---|---|
| CN | 1638650 | 7/2005 |
| JP | 2004-519241 | 7/2004 |
| JP | 2008-44945 | 2/2008 |
| JP | 2011-519362 | 7/2011 |
| JP | 2013-507394 | 3/2013 |
| JP | 2015-96475 | 5/2015 |
| JP | 2015-96555 | 5/2015 |
| JP | 5765832 | 8/2015 |
| JP | 2015-182954 A | 10/2015 |
| JP | 2016-509998 | 4/2016 |
| JP | 6013670 | 10/2016 |
| WO | 2009/050677 | 4/2009 |

OTHER PUBLICATIONS

Ueda, Takahiro et al., "Effects of Pediococcus acidilactici R037 on Serum Triglyceride Levels in Mice and Rats after Oral Administration", J. Nutr. Sci. Vitaminol., Feb. 28, 2018, vol. 64, pp. 41-47, abstract, fig. 2-3, table 1.
Chelliah, Ramachandran et al., "In vitro and in vivo defensive effect of probiotic LAB against Pseudomonas aeruginosa using Caenorhabditis elegans model", Virulence, Sep. 26, 2018, vol. 9, pp. 1489-1507, p. 1499, left column, line 1 to p. 1450, line 6, fig. 2.
Da Silva, Stéphanie et al., "Stress disrupts intestinal mucus barrier in rats via mucin O-glycosylation shift: prevention by a probiotic treatment", Am J Physiol Gastrointest Liver Physiol, 2014, vol. 307, pp. G420-G429.
Ait-Belgnaoui, Afifa et al., "Prevention of gut leakiness by a probiotic treatment leads to attenuated HPA response to an acute psychological stress in rats" Psychoneuroendocrinology, 2012, vol. 37, pp. 1885-1895.
International Search Report issued Dec. 17, 2019 in International (PCT) Application No. PCT/JP2019/038014.
Halami, P.M. et al., "*Lactobacillus farciminis* MD, a newer strain with potential for bacteriocin and antibiotic assay", Letters in Applied Microbiology, 2000, vol. 30, pp. 197-202.

* cited by examiner

*Primary Examiner* — Louise W Humphrey
*Assistant Examiner* — Alexander M Duryee
(74) *Attorney, Agent, or Firm* — Wenderoth, Lind & Ponack, L.L.P.

(57) ABSTRACT

The present invention provides a mitochondrial function-improving agent containing a lactic acid bacterium belonging to *Lactobacillus farciminis* or *Pediococcus acidilactici*, a culture of the lactic acid bacterium, or a culture supernatant of the lactic acid bacterium.

1 Claim, 5 Drawing Sheets

AGENT FOR IMPROVING MITOCHONDRIAL FUNCTION

TECHNICAL FIELD

The present invention relates to a mitochondrial function-improving agent.

BACKGROUND ART

From time immemorial, humankind has been known to have a thirst for immortality.

Even though immortality cannot be achieved, various methods are known as methods for extending lifespan. In particular, lifespan-extending agents, senescence retardants and the like which contain microorganisms such as lactic acid bacteria as active ingredients are known.

Patent Literature 1 discloses that a fermentation product obtained by fermenting a plant, which has been used extensively as a food, with lactic acid bacteria, yeast, *Aspergillus oryzae*, or the like suppresses various aging symptoms associated with advancing age and exhibits an effect of prolonging survival. In addition, it discloses that some of the fermentation products in the mixture of fermentation products used may be lactic acid fermentation products.

Patent Literature 2 discloses an invention relating to the use of intestinal bacteria to modify lymphoma penetrance and inflammation-mediated genotoxicity. It also discloses that the compositions and methods disclosed in Patent Literature 2 may be used to predict, treat and/or prevent illnesses including diseases associated with genome instability, to extend life expectancy, and to delay the onset of cancer.

Patent Literature 3 discloses a lifespan-extending agent containing a culture and/or bacterial cells obtained by culturing lactic acid bacteria belonging to *Bifidobacterium longum* as an active ingredient.

Patent Literature 4 discloses a lifespan-extending agent containing a culture and/or bacterial cells obtained by culturing lactic acid bacteria belonging to *Lactobacillus gasseri* as an active ingredient.

Patent Literature 5 discloses a lifespan-extending agent or senescence retardant characterized by containing a fermentation metabolite of the lactic acid bacterium *Lactococcus lactis* subsp. *cremoris* H-61 strain as an active ingredient.

CITATION LIST

Patent Literature

Patent Literature 1: Japanese Patent No. 6013670
Patent Literature 2: Japanese Translation of PCT International Application Publication No. 2016-509998
Patent Literature 3: Japanese Patent Laid-Open No. 2015-096555
Patent Literature 4: Japanese Patent No. 5765832
Patent Literature 5: Japanese Patent Laid-Open No. 2015-182954

SUMMARY OF INVENTION

Technical Problem

The problem to be solved by the present invention is to provide a novel food/drink material or medicament material having a lifespan-extending effect.

Solution to Problem

The present inventor has conducted intensive studies to solve the above problem and found that a novel lactic acid bacterium and a culture of the lactic acid bacterium can be a food/drink material or a medicament material having a lifespan-extending effect by improving mitochondrial function, thereby completing the present invention.

More specifically, the present invention is as follows.

(1) A mitochondrial function-improving agent comprising a lactic acid bacterium belonging to *Lactobacillus farciminis* or *Pediococcus acidilactici*, a culture of the lactic acid bacterium, or a culture supernatant of the lactic acid bacterium.

(2) The mitochondrial function-improving agent according to (1), wherein the mitochondrial function-improving agent is for improving metabolic function, extending lifespan, preventing aging, improving decreased athletic performance, suppressing muscle weakness, recovering from nervous system abnormalities, or improving cognitive function.

(3) A food, drink, supplement, medicament or cosmetic comprising the mitochondrial function-improving agent according to (1) or (2).

(4) A lactic acid bacterium being *Lactobacillus farciminis* OLL204082 strain (accession number: NITE BP-02635) or *Pediococcus acidilactici* OB7260 strain (accession number: NITE BP-02634).

The present invention also includes the following inventions.

(5) A method for improving mitochondrial function comprising a step of administering to a subject lactic acid bacteria belonging to *Lactobacillus farciminis* or *Pediococcus acidilactici*, a culture of the lactic acid bacteria, or a culture supernatant of the lactic acid bacteria.

(6) The method according to (5), wherein the method is for improving metabolic function, extending lifespan, preventing aging, improving decreased athletic performance, suppressing muscle weakness, recovering from nervous system abnormalities, or improving cognitive function.

(7) Use of a lactic acid bacterium belonging to *Lactobacillus farciminis* or *Pediococcus acidilactici*, a culture of the lactic acid bacterium, or a culture supernatant of the lactic acid bacterium, in production of a mitochondrial function-improving agent.

(8) The use according to (7), in the production of the mitochondrial function-improving agent for improving metabolic function, extending lifespan, preventing aging, improving decreased athletic performance, suppressing muscle weakness, recovering from nervous system abnormalities, or improving cognitive function.

(9) A lactic acid bacterium belonging to *Lactobacillus farciminis* or *Pediococcus acidilactici*, a culture of the lactic acid bacterium, or a culture supernatant of the lactic acid bacterium, for use in production of a mitochondrial function-improving agent.

(10) The lactic acid bacterium, the culture of the lactic acid bacterium, or the culture supernatant of the lactic acid bacterium according to (9), for use in the production of the mitochondrial function-improving agent for improving metabolic function, extending lifespan, preventing aging, improving decreased athletic performance, suppressing muscle weakness, recovering from nervous system abnormalities, or improving cognitive function.

(11) A lactic acid bacterium belonging to *Lactobacillus farciminis* or *Pediococcus acidilactici*, a culture of the lactic acid bacterium, or a culture supernatant of the lactic acid bacterium, for improving mitochondrial function.

(12) The lactic acid bacterium, the culture of the lactic acid bacterium, or the culture supernatant of the lactic acid bacterium according to (11), for improving metabolic function, extending lifespan, preventing aging, improving decreased athletic performance, suppressing muscle weakness, recovering from nervous system abnormalities, or improving cognitive function.

(13) Use of a lactic acid bacterium belonging to *Lactobacillus farciminis* or *Pediococcus acidilactici*, a culture of the lactic acid bacterium, or a culture supernatant of the lactic acid bacterium, for improving mitochondrial function.

(14) The use according to (13), for improving metabolic function, extending lifespan, preventing aging, improving decreased athletic performance, suppressing muscle weakness, recovering from nervous system abnormalities, or improving cognitive function.

(15) In the inventions (5) to (14), the mitochondrial function-improving agent may be used as a food, drink, supplement, medicament or cosmetic.

Advantageous Effects of Invention

According to the present invention, it is possible to provide a novel food/drink material or medicament material having a lifespan-extending effect.

BRIEF DESCRIPTION OF DRAWINGS

In FIGS. 1A to 1D, the MRS liquid medium treatment group (Cont (MRS medium)) is shown as a control. FIG. 1A shows the no treatment group (Untreated), FIG. 1B the *L. farciminis* OLL204082 strain treatment group (OLL204082), FIG. 1C the *P. acidilactici* OB7260 strain treatment group (OB7260), and FIG. 1D the *L. reuteri* MEP201805 strain treatment group (MEP201805) as a Comparative Example.

FIG. 3A shows the results of each lactic acid bacterium strain treatment group of *L. farciminis*, and FIG. 3B shows the results of each lactic acid bacterium strain treatment group of *P. acidilactici*.

DESCRIPTION OF EMBODIMENTS

Hereinafter, embodiments of the present invention will be described in detail. The present invention is not limited to the following embodiments, and can be modified in various ways within the scope of the gist thereof.

The mitochondrial function-improving agent of the present invention contains a lactic acid bacterium belonging to *Lactobacillus farciminis* or *Pediococcus acidilactici*, a culture of the lactic acid bacterium, or a culture supernatant of the lactic acid bacterium.

In the present description, the mitochondrial function-improving agent of the present invention containing a lactic acid bacterium belonging to *Lactobacillus farciminis* or *Pediococcus acidilactici* (hereinafter, sometimes collectively referred to "the lactic acid bacterium according to the present invention" in the present description) is not limited as long as it contains the lactic acid bacterium according to the present invention.

That is, the lactic acid bacterium according to the present invention may be contained as a suspension, or the lactic acid bacterium according to the present invention may be contained as an isolate.

In addition, a culture supernatant obtained by culturing the lactic acid bacterium according to the present invention may be contained.

In the present invention, the lactic acid bacterium belonging to *Lactobacillus farciminis* or *Pediococcus acidilactici* is not limited as long as it is a bacterium classified as *Lactobacillus farciminis* or *Pediococcus acidilactici* in accordance with the International Code of Nomenclature of Bacteria.

The *Lactobacillus farciminis* is not limited, and examples thereof include the *Lactobacillus farciminis* OLL204082 strain.

The *Pediococcus acidilactici* is not limited, and examples thereof include the *Pediococcus acidilactici* OB7260 strain.

*Lactobacillus farciminis* OLL204082 and *Pediococcus acidilactici* OB7260 are lactic acid bacteria which were internationally deposited on Feb. 14, 2018 (date of deposit) at NITE Patent Microorganisms Depositary (NPMD), Biological Resource Center, the National Institute of Technology and Evaluation (Room 122, 2-5-8, Kazusakamatari, Kisarazu-shi, Chiba, Japan) under the Budapest Treaty under the accession numbers NITE BP-02635 and NITE BP-02634, respectively.

In the present description, the mitochondrial function-improving agent of the present invention containing a culture of the lactic acid bacterium belonging to *Lactobacillus farciminis* or *Pediococcus acidilactici* (hereinafter, sometimes collectively referred to "the culture of the lactic acid bacterium according to the present invention" in the present description) is not limited as long as it contains the culture of the lactic acid bacterium according to the present invention.

The culture of the lactic acid bacterium according to the present invention may contain the lactic acid bacterium according to the present invention, or the lactic acid bacterium according to the present invention may be removed by a known method such as filtration, dialysis, precipitation, or centrifugation.

When the lactic acid bacterium according to the present invention is contained in the culture of the lactic acid bacterium according to the present invention, it may be contained as a live bacterium or it may be contained as a killed bacterium.

Moreover, the culture of the lactic acid bacterium according to the present invention may contain a medium component for culturing the lactic acid bacterium according to the present invention, or a part thereof may be removed.

The culture of the lactic acid bacterium according to the present invention may be contained as it is, may be contained as a concentrate, may be contained as a liquid, or may be contained as a solid.

The culture of the lactic acid bacterium according to the present invention may be a culture supernatant obtained by culturing the lactic acid bacterium according to the present invention. The mitochondrial function-improving agent of the present invention may contain a culture supernatant obtained by culturing the lactic acid bacterium according to the present invention.

In the present invention, the culture of the lactic acid bacterium according to the present invention is obtained by culturing the lactic acid bacterium according to the present invention.

The medium used for culturing the lactic acid bacterium according to the present invention is not limited. In addition, the method for culturing the lactic acid bacterium according to the present invention is not limited.

The mitochondrial function-improving agent according to the present invention can activate cells by improving mitochondrial function in cells with reduced mitochondrial function, and therefore can be used for purposes such as improving metabolic function, extending lifespan, preventing aging, improving decreased athletic performance, suppressing muscle weakness, recovering from nervous system abnormalities, and improving cognitive function.

The lactic acid bacterium according to the present invention, a culture thereof, and a culture supernatant thereof may be used to improve mitochondrial function.

The present invention may be a method for improving the mitochondrial function in a subject by administering to the subject the lactic acid bacterium according to the present invention, a culture thereof, and a culture supernatant thereof.

In the present invention, the lactic acid bacterium according to the present invention, a culture thereof, and a culture supernatant thereof may be administered to a subject and used for improving metabolic function, extending lifespan, preventing aging, improving decreased athletic performance, suppressing muscle weakness, recovering from nervous system abnormalities, or improving cognitive function in the subject.

The present invention may be a method for improving metabolic function, extending lifespan, preventing aging, improving decreased athletic performance, suppressing muscle weakness, recovering from nervous system abnormalities, or improving cognitive function in a subject by administering the lactic acid bacterium according to the present invention, a culture thereof, and a culture supernatant thereof to the subject.

The present invention may be a method for the treatment or prevention of diseases related to mitochondrial function in a subject by administering to the subject the lactic acid bacterium according to the present invention, a culture thereof, and a culture supernatant thereof.

Examples of the diseases related to mitochondrial function include metabolic dysfunction, short lifespan, aging, decreased athletic performance, muscle weakness, nervous system abnormalities, and cognitive decline.

The mitochondrial function-improving agent according to the present invention can be used as a food, drink, supplement, medicament or cosmetic.

The food, drink, supplement, medicament or cosmetic may be for humans, or it may be for pets or livestock.

In the present description, the medicament is a concept including quasi drugs. In addition, in the present description, the cosmetic may be a medicated cosmetic containing the lactic acid bacterium according to the present invention, a culture thereof, and a culture supernatant thereof.

In the present invention, the mitochondrial function-improving agent may be used in combination with other components used for purposes such as improving metabolic function, extending lifespan, preventing aging, improving decreased athletic performance, suppressing muscle weakness, recovering from nervous system abnormalities, and improving cognitive function.

The other components can be appropriately selected.

When the mitochondrial function-improving agent of the present invention is used as a cosmetic, its form is not limited and may be an emulsion, a cream, an aqueous solution, a pack or the like.

The cosmetic composition may contain various components used in cosmetics. The various components are not limited, but examples thereof include oily components, emulsifiers, moisturizing agents, thickeners, medicinal components, preservatives, pigments, powders, pH adjusters, ultraviolet absorbers, antioxidants and fragrances, and the blending amount thereof is not limited.

When the mitochondrial function-improving agent according to the present invention is used as a medicament (including quasi-drugs), it can be administered orally or parenterally as a drug, a pharmaceutical preparation and/or a pharmaceutical composition.

For oral administration, known dosage forms for administration such as tablets, capsules, coated tablets, lozenges, liquid preparations such as solutions or suspensions can be used.

Parenteral administration includes intravenous, intramuscular or subcutaneous administration by injection, transmucosal administration such as in the nasal cavity or oral cavity using a powder, drops, a spray, an aerosol, etc., rectal administration using a cream, suppository, etc., and transdermal administration using a patch, liniment, gel, etc.

The route of administration is preferably oral administration or intravenous administration by injection.

When the mitochondrial function-improving agent according to the present invention is used as a pharmaceutical preparation and/or a pharmaceutical composition, it may contain an appropriate and pharmaceutically acceptable carrier well known to those skilled in the art, depending on the administration form and the like, as appropriate.

The pharmaceutically acceptable carrier is not limited, and examples thereof include antioxidants, stabilizers, preservatives, flavoring agents, colorants, dissolving agents, solubilizers, surfactants, emulsifiers, antifoamers, viscosity adjusting agents, gelling agents, absorption promoters, dispersants, excipients and pH adjusters.

In the present invention, the dose and dosage regimen of the lactic acid bacterium according to the present invention, the culture thereof, and the culture supernatant thereof may be adjusted depending on the required amount, treatment method, the degree of illness or necessity for each individual treatment subject.

The dose can be determined specifically according to age, body weight, general health condition, gender, diet, administration time, administration method, excretion rate, drug combination, patient's medical condition, and the like, and furthermore, may be determined in consideration of other factors.

It is preferable that the lactic acid bacterium according to the present invention, the culture thereof, and the culture supernatant thereof be contained in an amount effective in exerting a desired effect.

The daily dose of the lactic acid bacterium according to the present invention, the culture thereof, and the culture supernatant thereof varies depending on the condition and body weight of the subject, the type of compound, the route of administration, and the like. In the case of parenteral administration, it is usually about 0.01 to 1000 mg/person/day, preferably 0.1 to 500 mg/person/day, and in the case of oral administration, it is usually about 0.01 to 5000 mg/person/day, preferably 0.1 to 3000 mg/person/day.

When the lactic acid bacterium according to the present invention, a culture thereof, and a culture supernatant thereof are administered to a subject in need thereof, the subject in need thereof is not limited, and is mammalian (also referred to as a mammal) or avian, preferably a human, but may be a pet, livestock, or the like.

The subject may have a disease related to mitochondrial function, such as mitochondrial malfunction or mitochondrial dysfunction.

When the mitochondrial function-improving agent of the present invention is used as a food or drink, its form is not limited. For example, in the present invention, it is suitable to use the mitochondrial function-improving agent of the present invention as a dietary supplement or a supplement.

When the mitochondrial function-improving agent of the present invention is used as a food or drink, the daily dose of the lactic acid bacterium according to the present invention, the culture thereof, and the culture supernatant thereof varies depending on the condition and body weight of the subject, the type of compound, the route of administration, and the like, but is usually about 10 to 1000 g/person/day, preferably 50 to 200 g/person/day.

The food/drink composition may contain various components used in foods and drinks. The various components are not limited, but examples thereof include oily components, emulsifiers, moisturizing agents, thickeners, pharmaceutical components, preservatives, pigments, powders, pH adjusters, ultraviolet absorbers, antioxidants and fragrances, and the blending amount thereof is not limited.

As a food or drink, for example, it can be used as a fermented food or drink such as fermented tea, fermented milk, yogurt, lactic acid bacteria beverages, fermented sausage, cheese, miso, kimchi, nukazuke, and shio koji.

In the present invention, the mitochondrial function-improving agent of the present invention can be used for pets, and is suitably used as pet cosmetics, pet medicaments, pet food, and pet foods and drinks such as dietary supplements/supplements for animals such as mammals and birds. In addition, the mitochondrial function-improving agent of the present invention can be used for livestock, and can also be used as livestock cosmetics, livestock medicaments, and livestock foods and drinks such as livestock feed.

In the present invention, the pet and the livestock are not limited. Examples thereof include dogs, cats, birds, rabbits, guinea pigs, goats, cows, horses, and pigs, and they may be reptiles and amphibians.

EXAMPLES

Hereafter, the present invention is further described specifically with Examples, but the present invention is not limited to these Examples. In addition, various changes can be made without deviating from the technical idea of the present invention.

Example 1

(1) Preparation of Lactic Acid Bacterium Culture

A *Lactobacillus farciminis* OLL204082 strain, *Pediococcus acidilactici* OB7260 strain, and *Lactobacillus reuteri* MEP201805 strain were each cultured for 18 hours under anaerobic conditions by ANAERO PACK® ("ANAERO PACK® Kenki", an anaerobic cultivation system manufactured by MITSUBISHI GAS CHEMICAL COMPANY, INC.) in MRS liquid medium ("Lactobacilli MRS Broth", Product number: #288130, manufactured by Difco Laboratories). The culture temperature was 30° C. for the OLL204082 and OB7260 strains, and 37° C. for the MEP201805 strain. After centrifuging 5 mL of the culture solution at 2330 g for 10 minutes, 4.25 mL of the supernatant was removed. The precipitate was suspended in the remaining supernatant to obtain the product to be administered to mice. In addition, MRS liquid medium was also used for administration as a control.

(2) Animal Test

Ndufs4 (NADH dehydrogenase iron-sulfur protein 4) KO mice prepared according to Cell Metabolism 7, 312-320 (2008) were grouped as follows. The number n in each group is also shown.

For 4 weeks, from the time of weaning (about 3 weeks) to 50 days after birth, a culture of lactic acid bacteria or MRS liquid medium was administered to each group. The dose was 150 µL/body/day, the administration frequency was 5 to 6 times a week, and the administration method was oral gavage administration using a stomach tube.

1. No treatment group (Untreated) (n=11)
2. MRS liquid medium treatment group (control) (n=6)
3. *L. farciminis* OLL204082 strain treatment group (n=8)
4. *P. acidilactici* OB7260 strain treatment group (n=7)
5. *L. reuteri* MEP201805 strain treatment group (Comparative Example) (n=6)

(3) Evaluation Items

Figure 1:
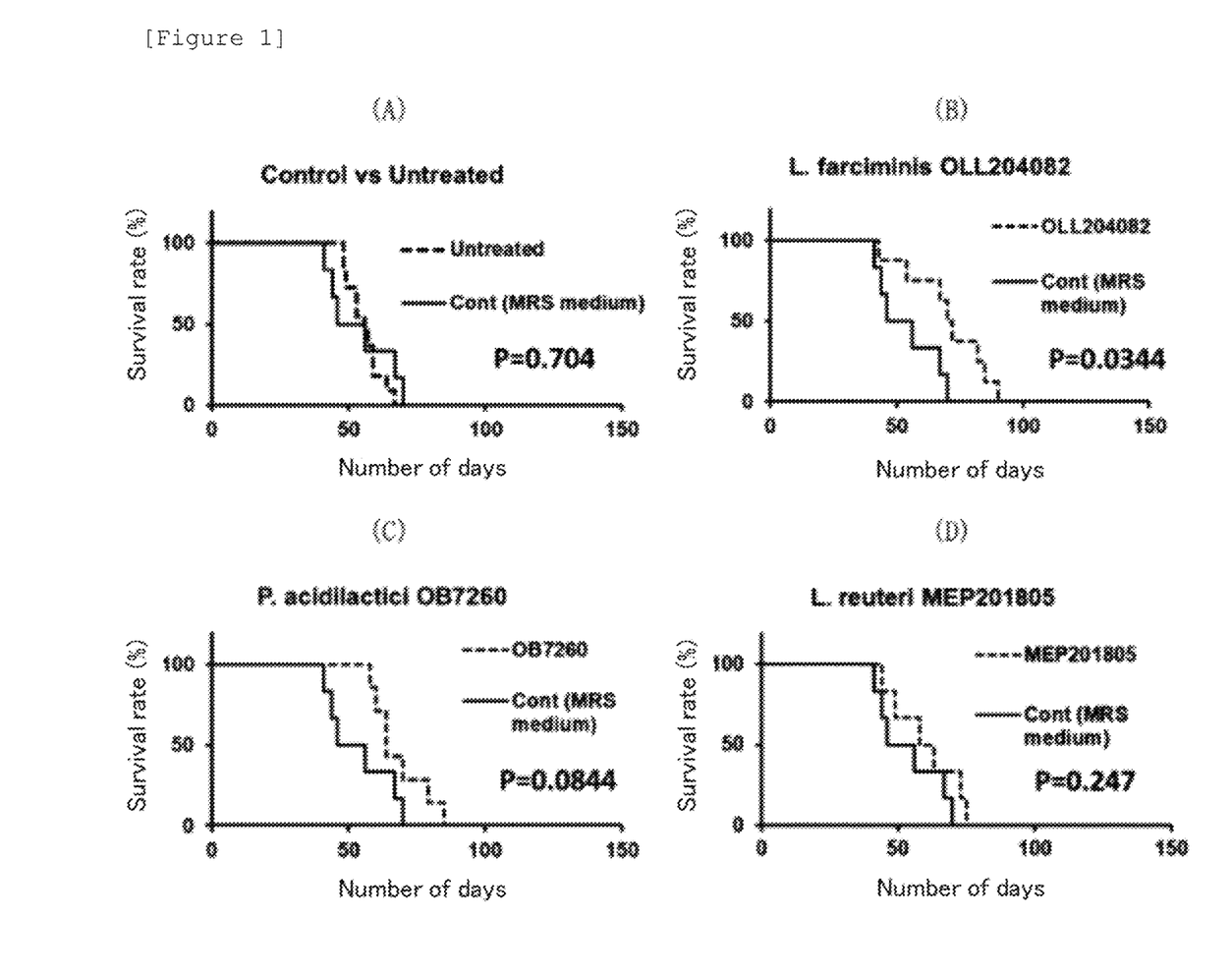
FIG. 1 shows the effect of the administration of a culture of lactic acid bacteria on the lifespan of animals in Example 1. On the survival curve, the vertical axis indicates the survival rate (%) and the horizontal axis indicates the number of days after birth.
Figure 2:
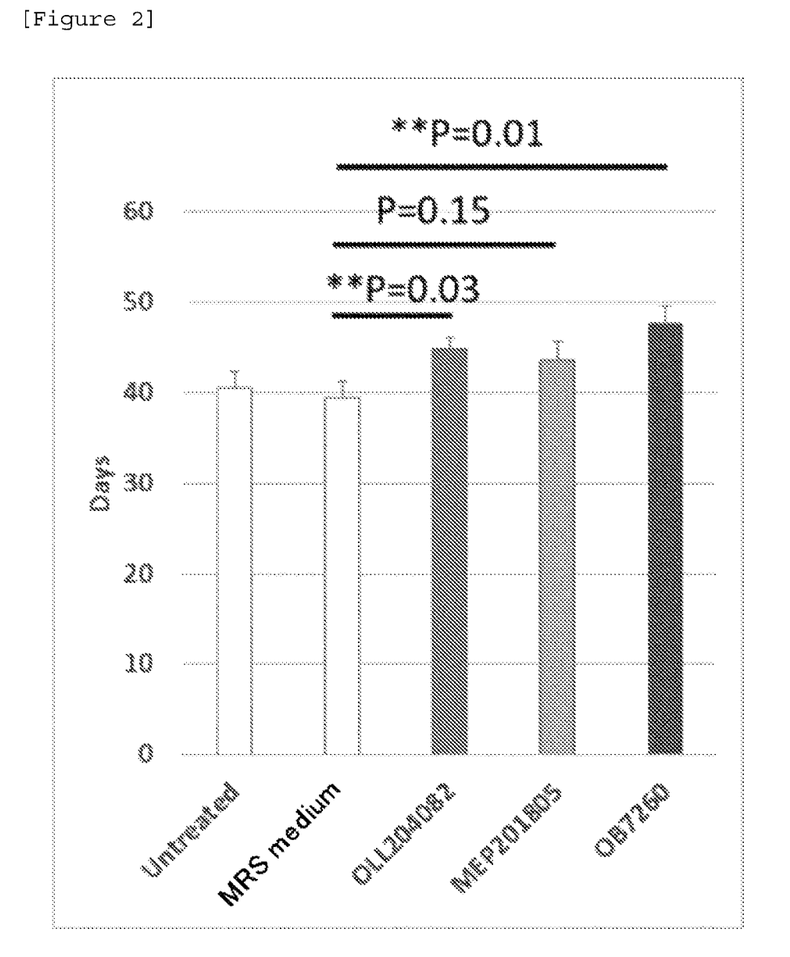
FIG. 2 shows the number of days after birth until the occurrence of clasping by the administration of a culture of lactic acid bacteria in Example 1.

The number of days after birth until the mouse died and the number of days after birth until the occurrence of clasping were measured. The measurement results are shown in FIGS. 1 and 2, respectively. Clasping is a characteristic behavior of mice associated with the progress of neurological abnormalities (Food Funct., 4, 1776-1793 (2013)).

(4) Statistical Analysis

The online site Oasis2 (Online Application for Survival Analysis 2) was used for the statistical analysis.

Results

The lifespan of Ndufs4 KO mice was significantly extended by the administration of the culture of the *L. farciminis* OLL204082 strain or the culture of the *P. acidilactici* OB7260 strain, as compared with the MRS liquid medium treatment group (control) (FIG. 1, P=0.0344, 0.0844 T-TEST).

In addition, the occurrence of clasping was significantly delayed by the administration of the culture of the *L. farciminis* OLL204082 strain or the culture of the *P. acidilactici* OB7260 strain, as compared with the MRS liquid medium treatment group (control) (FIG. 2, P=0.03, 0.01 T-TEST).

On the other hand, the administration of the culture of the *L. reuteri* MEP201805 strain had no significant effect on the extension of lifespan and the occurrence time of clasping (FIG. 1, p=0.247 T-TEST, and FIG. 2, p=0.15 T-TEST).

The Ndufs4 KO mouse is a model mouse in which mitochondria are dysfunctional. Since the lifespan of the mice was extended by administration of the culture of the *L.* farciminis OLL204082 strain or the culture of the *P. acidilactici* OB7260 strain, these lactic acid bacteria strains can be considered to have an effect of improving mitochondrial function.

Example 2

The effect of administration of a plurality of lactic acid bacteria strains on the lifespan of mitochondrial disease model mice was confirmed.
(1) Preparation of Lactic Acid Bacterium Culture With reference to Example 1, each lactic acid bacterium strain was cultured in MRS liquid medium overnight at 30° C. under anaerobic conditions by ANAERO PACK®. After centrifuging 2 mL of the culture solution at 2330 g for 10 minutes, 1.7 mL of the supernatant was removed. The precipitate was suspended in the remaining supernatant to obtain the product to be administered to mice. For only the OB7260 strain, in addition to the above-mentioned administration product, another administration product was also prepared by completely removing the supernatant after centrifuging the culture solution, and then suspending the precipitate in 0.3 mL of phosphate buffered saline (PBS) (hereinafter, OB7260 strain PBS suspension).
(2) Animal Test With reference to Example 1, for 4 weeks, from the time of weaning of the Ndufs4 KO mouse (about 3 weeks) to 65 days after birth, a culture of lactic acid bacteria or MRS liquid medium was administered to each group. The dose was 300 µL/body/day, the administration frequency was 5 to 6 times a week, and the administration method was oral gavage administration using a stomach tube.
  1. No treatment group (Untreated) (n=20)
  2. MRS liquid medium treatment group (control) (n=13)
  3. *L. farciminis* OLL204082 strain treatment group (n=12)
  4. *L. farciminis* P1804501 strain treatment group (n=10)
  5. *L. farciminis* P1804502 strain treatment group (n=7)
  6. *P. acidilactici* OB7260 strain treatment group (n=11)
  7. *P. acidilactici* P1804503 strain treatment group (n=9)
  8. *P. acidilactici* P1804504 strain treatment group (n=9)
  9. *P. acidilactici* OB7260 strain PBS suspension treatment group (n=8)

Figure 3:
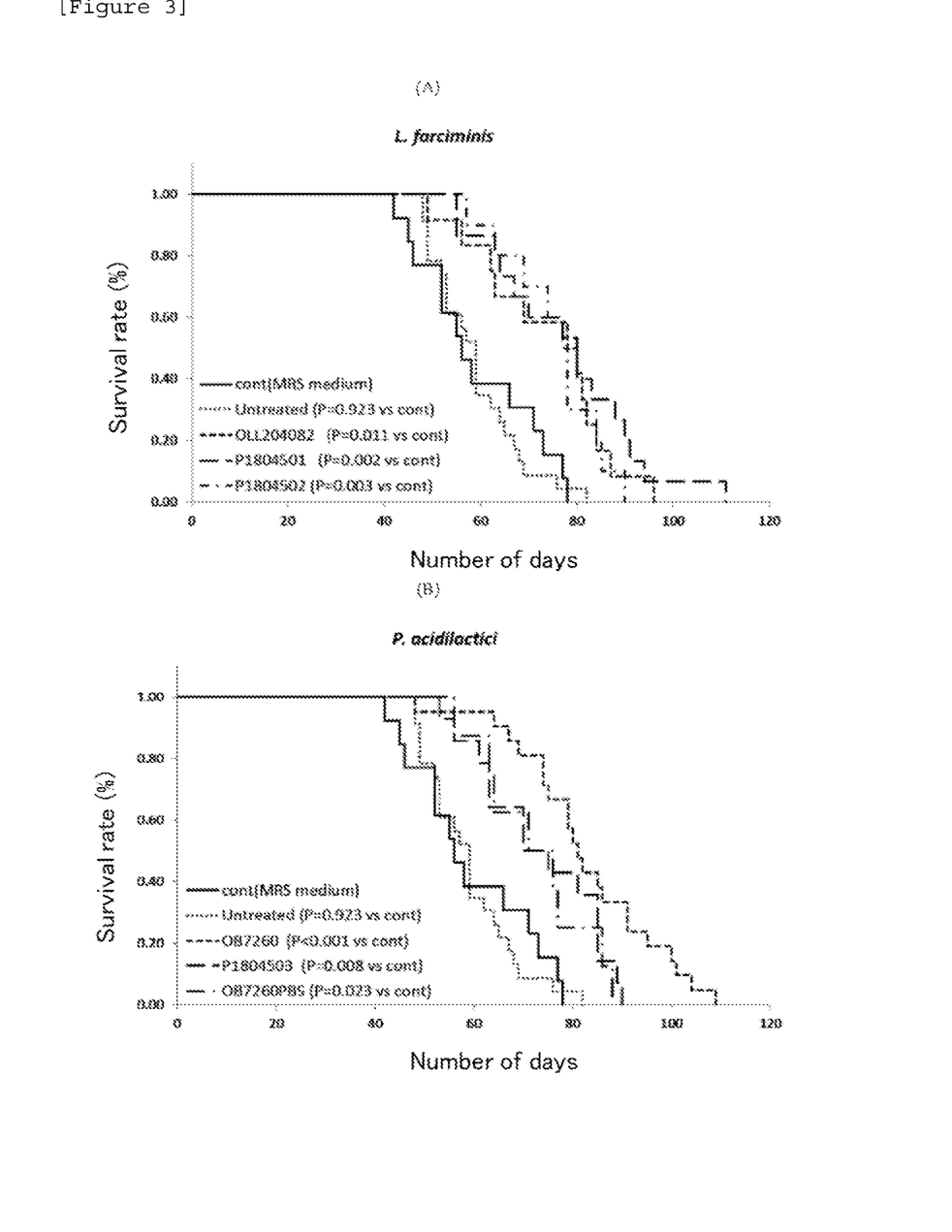
FIG. 3 shows the effect of the administration of a culture of lactic acid bacteria on the lifespan of animals in Example 2. On the survival curve, the vertical axis indicates the survival rate (based on 1.00) and the horizontal axis indicates the number of days after birth.
Figure 4:
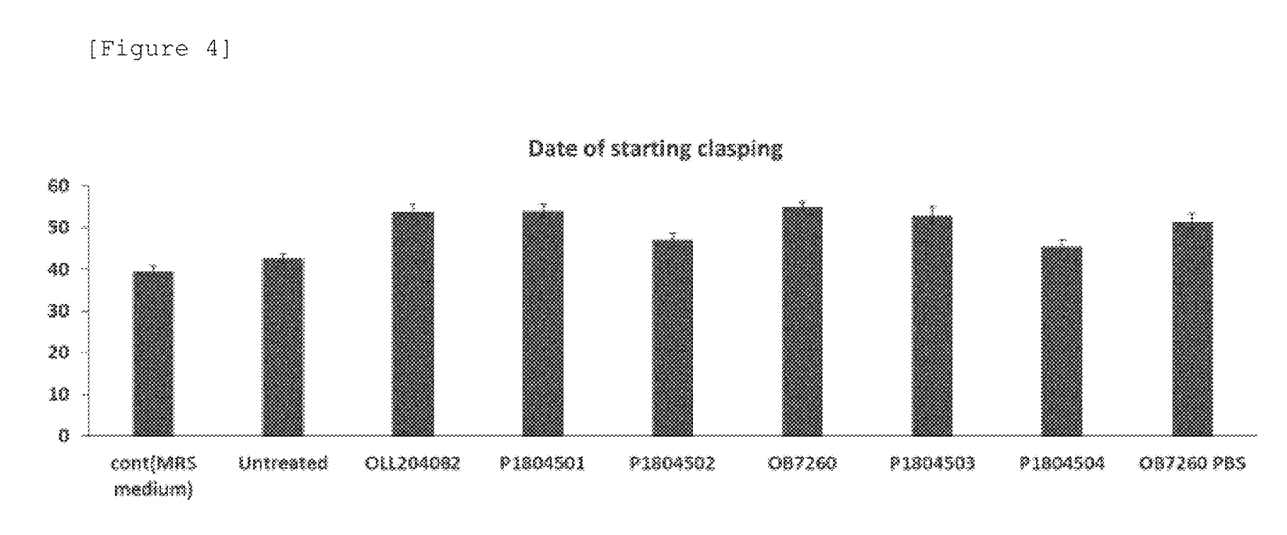
FIG. 4 shows the number of days after birth until the occurrence of clasping by the administration of a culture of lactic acid bacteria in Example 2.

The *L. farciminis* P1804501 strain, the *L. farciminis* P1804502 strain, the *P. acidilactici* P1804503 strain and the *P. acidilactici* P1804504 strain are lactic acid bacteria strains obtained by isolation from raw milk, and stored at Meiji Co., Ltd.
(3) Evaluation Items The number of days after birth until the mouse died and the number of days after birth until the occurrence of clasping were measured. The measurement results are shown in FIGS. 3 and 4, respectively.
(4) Results The lifespan of Ndufs4 KO mice was significantly extended by the administration of the culture of each lactic acid bacterium strain or the OB7260 strain PBS suspension, as compared with the MRS liquid medium treatment group (control) (FIG. 3).

In addition, the occurrence of clasping was significantly delayed by the administration of the culture of each lactic acid bacterium strain or the PBS suspension, as compared with the MRS liquid medium treatment group (control) (FIG. 4, $p<0.05$ (T-TEST)).

Since the lifespan of mice was extended by the administration of the cultures of not only the *L. farciminis* OLL204082 strain and the *P. acidilactici* OB7260 strain, but also of other lactic acid bacteria strains of *L. farciminis* and *P. acidilactici*, the lactic acid bacteria belonging to *L. farciminis* and *P. acidilactici* can be considered to have an effect of improving mitochondrial function.

As described above, the lifespan of the OB7260 strain culture treatment group and the OB7260 strain PBS suspension treatment group were both significantly extended, as compared with the MRS liquid medium treatment group (control). Of these two groups, the lifespan was extended significantly more with the culture treatment group, with an average lifespan of 82.6 days for the culture treatment group, and 72.6 days with the PBS suspension ($P=0.096$ T-TEST). Hence, it is considered that the precipitate formed by centrifuging the culture of OB7260 (which is mainly composed of live cells of OB7260) has a mitochondrial improving function, since the lifespan is extended in the PBS suspension treatment group. Furthermore, since the lifespan was extended significantly more with the culture, which is a mixture of the precipitate and the supernatant, than the PBS suspension, it was considered that the supernatant also has a mitochondrial improving function.

Example 3

Since mitochondrial dysfunction is known to be associated with skeletal muscle aging, skeletal muscle abnormalities, and sarcopenia, the effect on muscle weakness due to aging in healthy aged mice was confirmed.
(1) Preparation of Lactic Acid Bacterium Culture Similarly as in Example 2, the *P. acidilactici* OB7260 strain was cultured in MRS liquid medium overnight at 30° C. under anaerobic conditions by ANAERO PACK®. After centrifuging 2 mL of the culture solution at 2330 g for 10 minutes, 1.7 mL of the supernatant was removed. The precipitate was suspended in the remaining supernatant to obtain the product to be administered to mice.
(2) Animal Test A culture of lactic acid bacteria was administered to 22 to 24-month-old healthy aged C57BL6J mice (male) for 2 months (n=12). A non-administered group was set as the control. The grip strength was measured 16 days after the end of the administration period.
(3) Evaluation Items (Measurement of Grip Strength)

Figure 5:
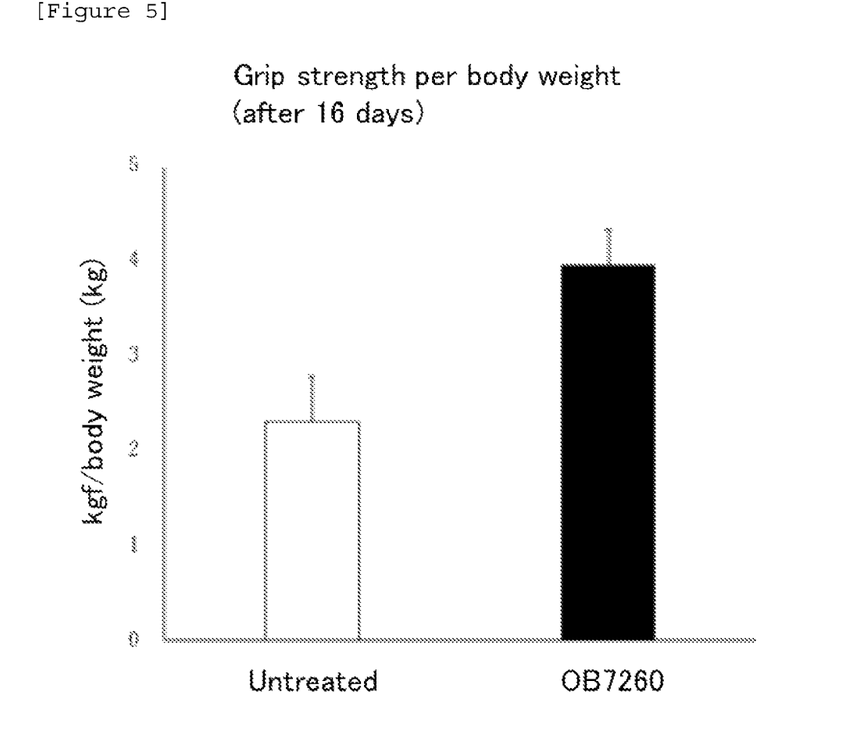
FIG. 5 shows the effect of the administration of a culture of *P. acidilactici* OB7260 strain on grip strength per body weight.

The tail was pulled horizontally 10 times per animal, and the grip strength at that time was measured with a rat/mouse grip strength meter (Muromachi Kikai Co., Ltd., MK-380CM/F), of which the maximum value was recorded. The maximum value of grip strength was divided by the body weight to calculate the grip strength per body weight (kgf/body weight). The results are shown in FIG. 5.
(4) Results The grip strength per body weight of aged mice was significantly higher in the group administered with a culture of the *P. acidilactici* OB7260 strain, than in the no treatment group (Untreated) ($p<0.05$, T-TEST).

The invention claimed is:

1. A method for improving mitochondrial function, comprising: administering a therapeutically effective amount of a lactic acid bacterium belonging to *Lactobacillus farciminis* or *Pediococcus acidilactici*, or a culture of the lactic acid bacterium, to a subject in need thereof, wherein the *Lactobacillus farciminis* is *Lactobacillus farciminis* OLL204082 strain, accession number: NITE BP-02635, or the *Pediococcus acidilactici* is *Pediococcus acidilactici* OB7260 strain, accession number: NITE BP-02634.

* * * * *